United States Patent [19]
Buck et al.

[11] Patent Number: 5,397,452
[45] Date of Patent: Mar. 14, 1995

[54] REFERENCE ELECTRODE

[75] Inventors: Michael D. Buck, Loveland; Steven Zelenak, Bellvue; John R. Dunkle, Fort Collins; Gary W. Johnson, Loveland; James D. McWilliams, Windsor, all of Colo.

[73] Assignee: Hach Company, Loveland, Colo.

[21] Appl. No.: 250,551

[22] Filed: May 27, 1994

[51] Int. Cl.6 .......................................... G01N 27/26
[52] U.S. Cl. .................................. 204/435; 204/433; 204/420; 204/414
[58] Field of Search ............... 204/435, 433, 420, 414, 204/413

[56] References Cited

U.S. PATENT DOCUMENTS 3,188,285  6/1965  Watanabe et al. ............... 204/420

Primary Examiner—John Niebling
Assistant Examiner—Bruce F. Bell
Attorney, Agent, or Firm—Dean P. Edmundson

[57] ABSTRACT

A reference electrode including a body, a supply of flowable gel electrolyte, a wire electrode, and a tube for the electrolyte. The electrolyte is preferably contained in a cartridge within the body of the electrode and is capable of being dispensed into the tube in very small, metered, amounts, as needed.

7 Claims, 10 Drawing Sheets

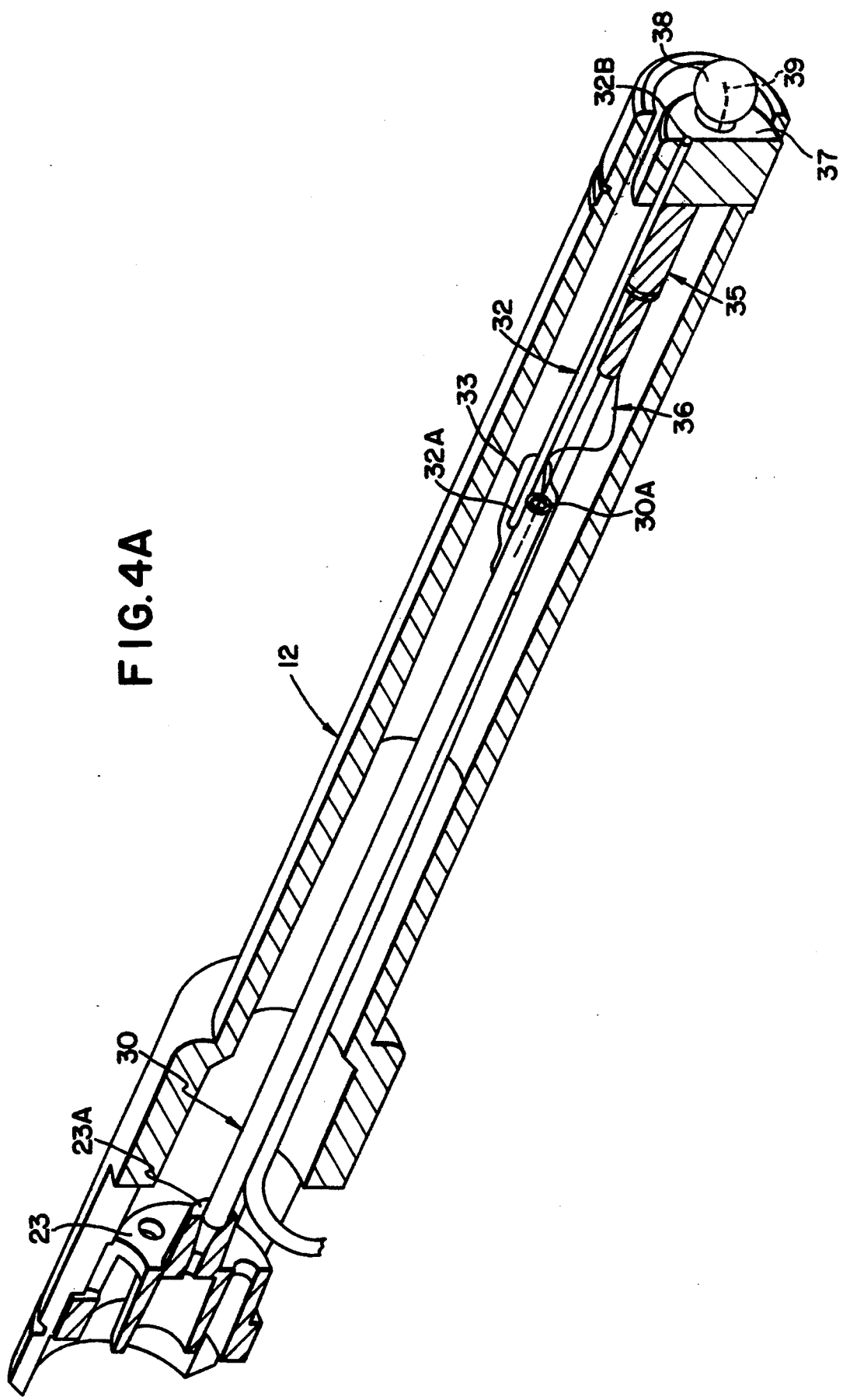

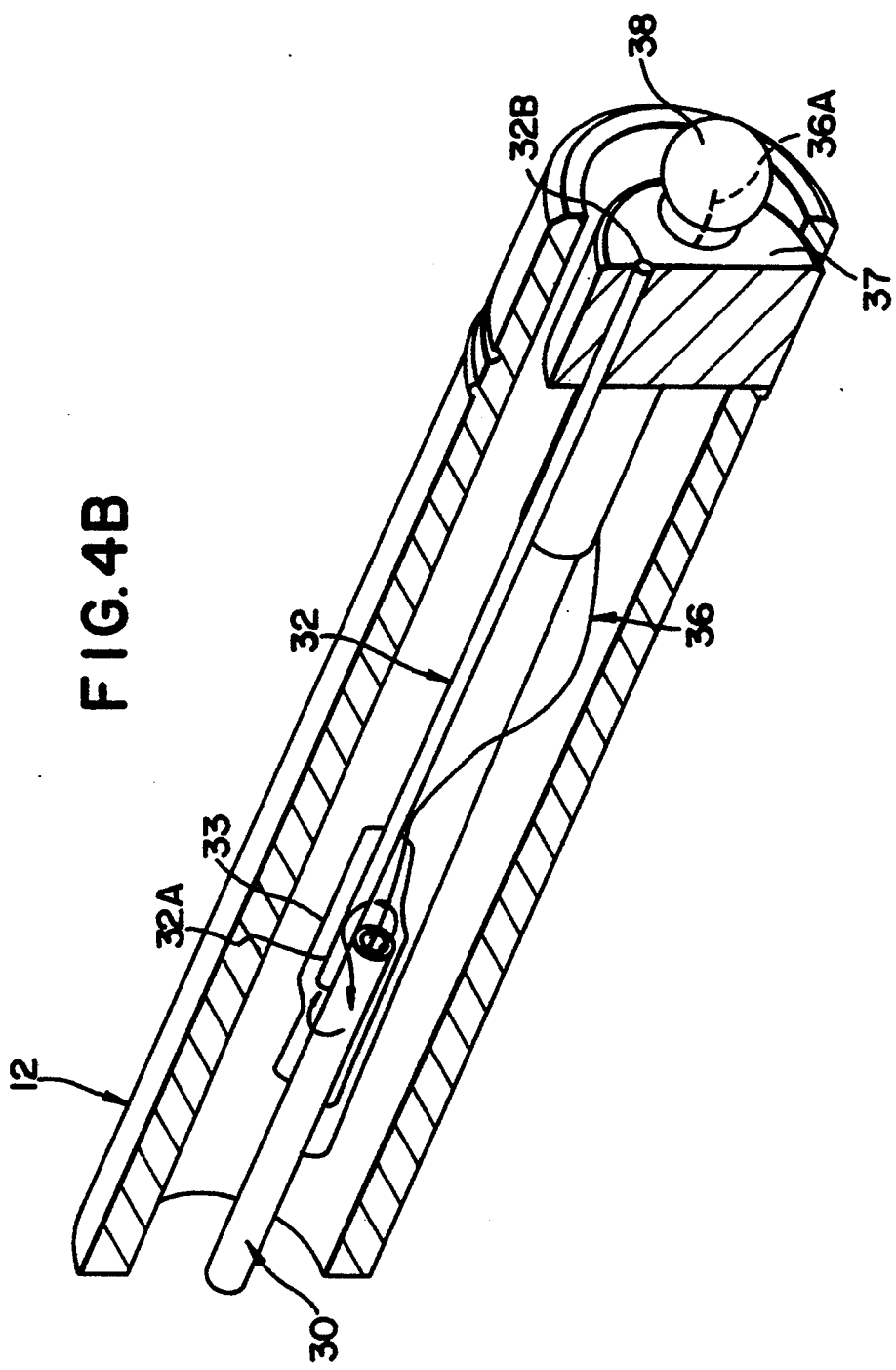

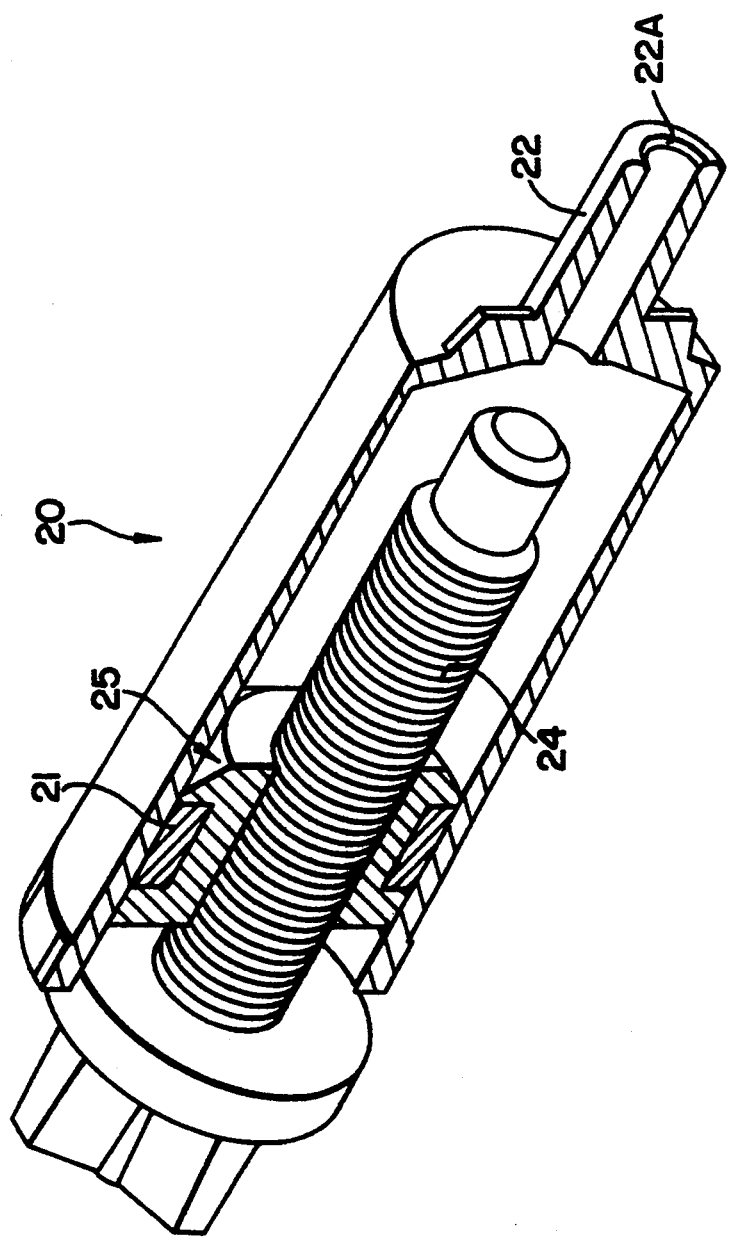

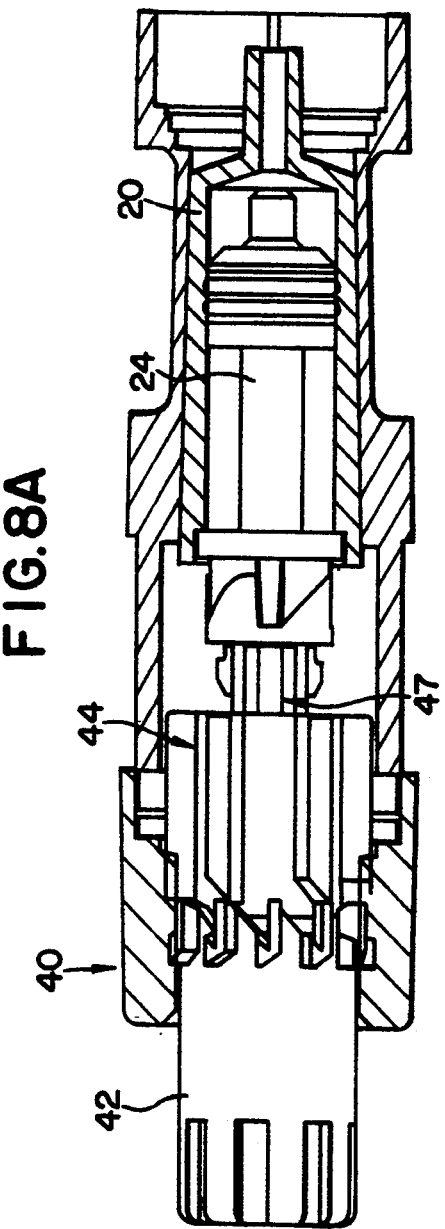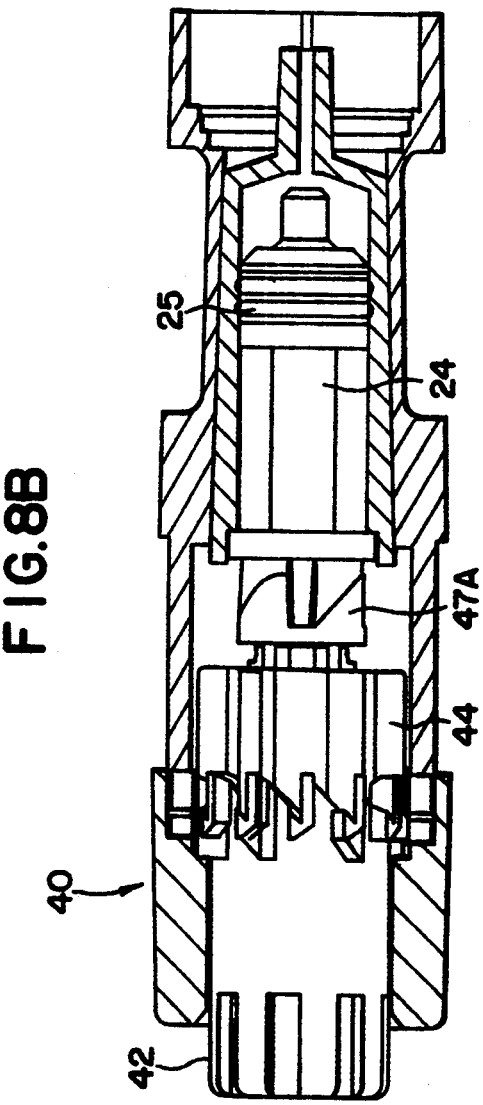

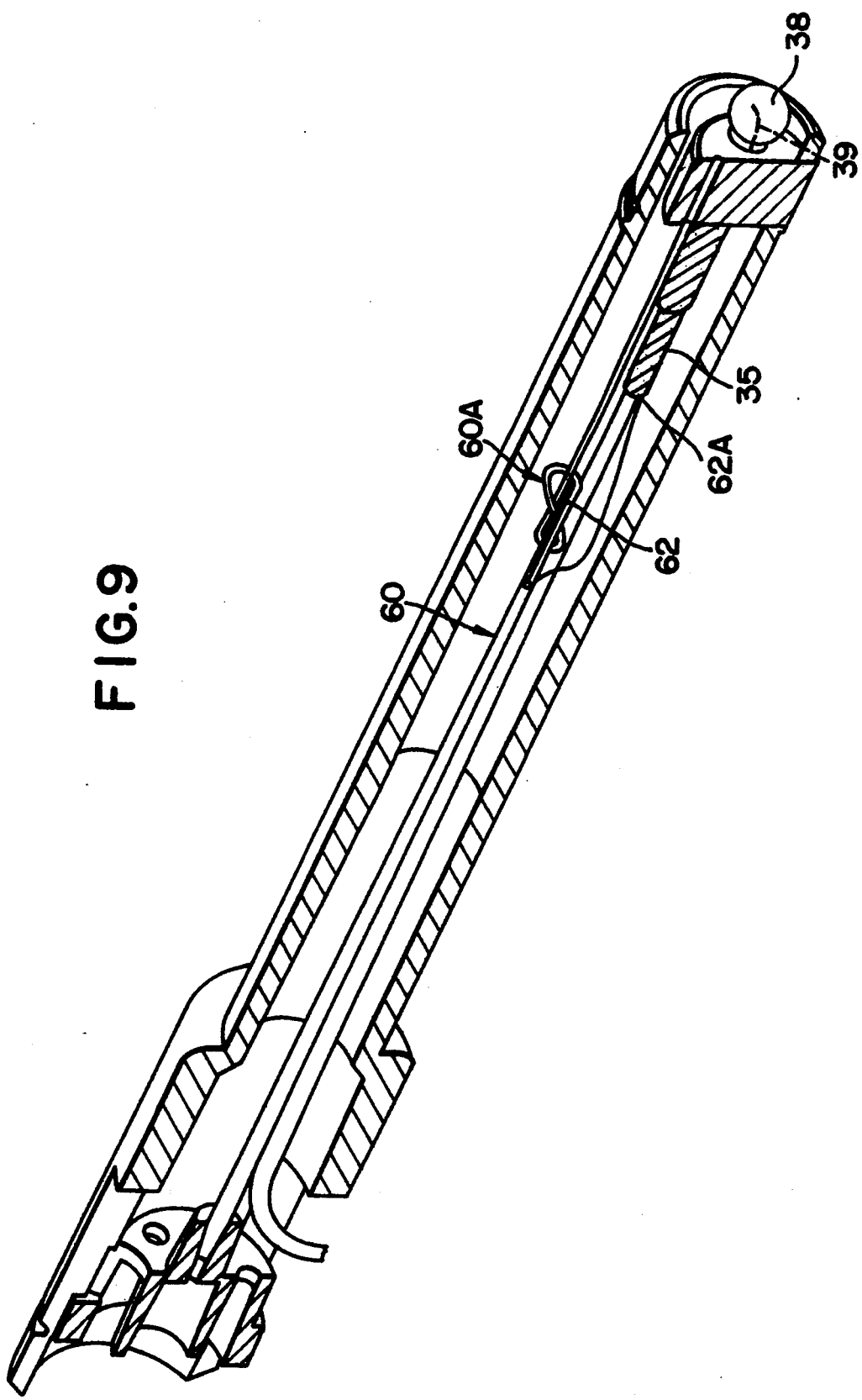

REFERENCE ELECTRODE

FIELD OF THE INVENTION

This invention relates to reference electrodes for use in scientific laboratory instruments. More particularly, this invention relates to reference electrodes having a free-flowing junction. Even more particularly, this invention relates to laboratory reference electrodes for use with pH or ISE potentiometric sensors.

BACKGROUND OF THE INVENTION

Conventional reference electrodes have limited lifetimes due to contamination of the internal reference elements by the sample or by fouling of the restriction devices which are used to control the flow of reference electrolyte from the interior of the electrode into the sample. For example, typical restriction devices used in electrodes include porous glass or plastic frits, sleeve joints, ion exchange membranes, etc. Such conventional reference electrodes exhibit large offsets, unpredictable temperature coefficients and/or unstable potential readings after short periods of usage.

In conventional electrodes, the liquid sample can diffuse past the restriction device and into the reference electrolyte (which may be a liquid, gel, or polymer substance). This diffusion cannot be completely reversed, and eventually sample constituents will reach the reference element, potentially poisoning it.

Some manufacturers have been able to slow down contamination of the internal reference elements by using double junction references, allowing the reference electrolyte to be replaced periodically. However, this is a cumbersome process and does not address the problem of fouling of the restriction device.

Free flowing reference outlets can be used instead of restriction devices to prevent fouling. With a free flowing reference outlet the reference electrolyte and sample solution form an interface where ions are free to flow between the two solutions. There are no physical barriers, except for the limited exposed surface area of the junction, to impede the flow of electrolyte into the sample (and vice versa). Unrestricted flow offers the best possible means of minimizing reference junction potentials caused by fouling, but can lead to problems of excessive reference electrolyte leakage, thus contaminating the sample.

The Orion brand "Sure Flow" device (and others of similar type) uses a ground glass seat and seal in a reference electrode. The seal consists of the glass reference bulb. In normal operation of such device the liquid electrolyte seeps through this seal. The glass reference is prone to clogging and contamination by the sample being tested. To renew and clean the reference, the user presses the top of the electrode to cause the bulb to separate from the seat. This allows the low viscosity electrolyte to flow through the open seal (by gravity feed), flushing the surface of the bulb clear of contamination. This is a very uncontrolled process for cleaning the glass bulb. Not only can the surfaces not be washed clean at times, but the entire reservoir of electrolyte can be quickly used for this cleaning function. Thus, the entire supply of electrolyte can be rapidly exhausted.

Other problems which can be encountered with reference electrodes of the type which include a hollow tube to supply liquid electrolyte. For example, the tube can become pinched, broken or clogged. A high leakage rate through the tube has also been observed. Also, problems interfering with flow of electrolyte can be caused by failure of the connectors used.

There has not heretofore been provided a reference electrode having the advantages provided by the present invention.

SUMMARY OF THE PRESENT INVENTION

In accordance with the present invention there is provided an improved reference electrode which, in one embodiment comprises:
  (a) an elongated body member,
  (b) an elongated tube supported by said body member; said tube including first and second ends; wherein said tube includes a flow loop of at least 360° between the first and second ends; wherein the second end is open;
  (c) a reference element positioned in the tube; and
  (d) a supply of flowable gel electrolyte which is in communication with the first end of the tube; wherein the electrolyte fills the tube and is in contact with the reference element; and wherein the electrolyte can be urged through the tube and out through the second end of the tube.

The improved reference electrode avoids the typical problems associated with conventional reference electrodes and exhibits extended lifetimes. Thus, the reference electrode of the invention utilizes a flowable gel electrolyte in a tube having an open end. A reservoir of gel electrolyte is contained in a cartridge from which it can be dispensed in very small and precisely-metered amounts into the tube.

Preferably the gel electrolyte is a water-soluble, non-ionic, pseudoplastic gel. Use of such a gel electrolyte, when dispensed between sample measurements, solves the problems associated with conventional restriction devices, such as fouling, sample contamination, and reference element contamination.

The water solubility and pseudoplastic nature of the gel allow it to be pumped and rinsed, thus enabling contaminants to be expelled to waste between sample measurements. The non-ionic nature of the gel prevents it from interfering with ion flow (migration), which could cause unpredictable junction potentials. The high viscosity of the gel slows down diffusion flux of ions into and out of the sample solution by causing the movement of ions to be less affected by convective forces, thus reducing contamination. By using small bore tubing to deliver the gel, contamination of the sample and reference element due to convection is reduced.

Thus, the reference electrode of the invention utilizes a renewable junction and achieves a very desirable balance between unrestricted flow of electrolyte and non-fouling characteristics. In other words, the novel reference electrode includes a renewable restriction device. The invention provides a less cumbersome means of implementing a free flowing reference outlet, without the problems of high leakages rates.

Other advantages of the reference electrode of the present invention will be apparent from the following detailed description and the accompanying drawings.

BRIEF DESCRIPTION OF THE DRAWINGS

The invention is described in more detail hereinafter with reference to the accompanying drawings, wherein like reference characters refer to the same parts throughout the several views and in which:

FIG. 4A is a cut-away view of the electrode shown in FIG. 1;

FIG. 4B is a cut-away view of the lower portion of the reference electrode in FIG. 1;

FIG. 7 is a cut-away view of one embodiment of electrolyte cartridge useful in the reference electrode;

FIG. 8A is a cut-away view showing the actuator mechanism in one position;

FIG. 8B is a cut-away view showing the actuator mechanism in another position; and FIG. 9 is a cut-away view showing another embodiment of electrode of the invention.

DETAILED DESCRIPTION OF THE INVENTION

Figure 1:
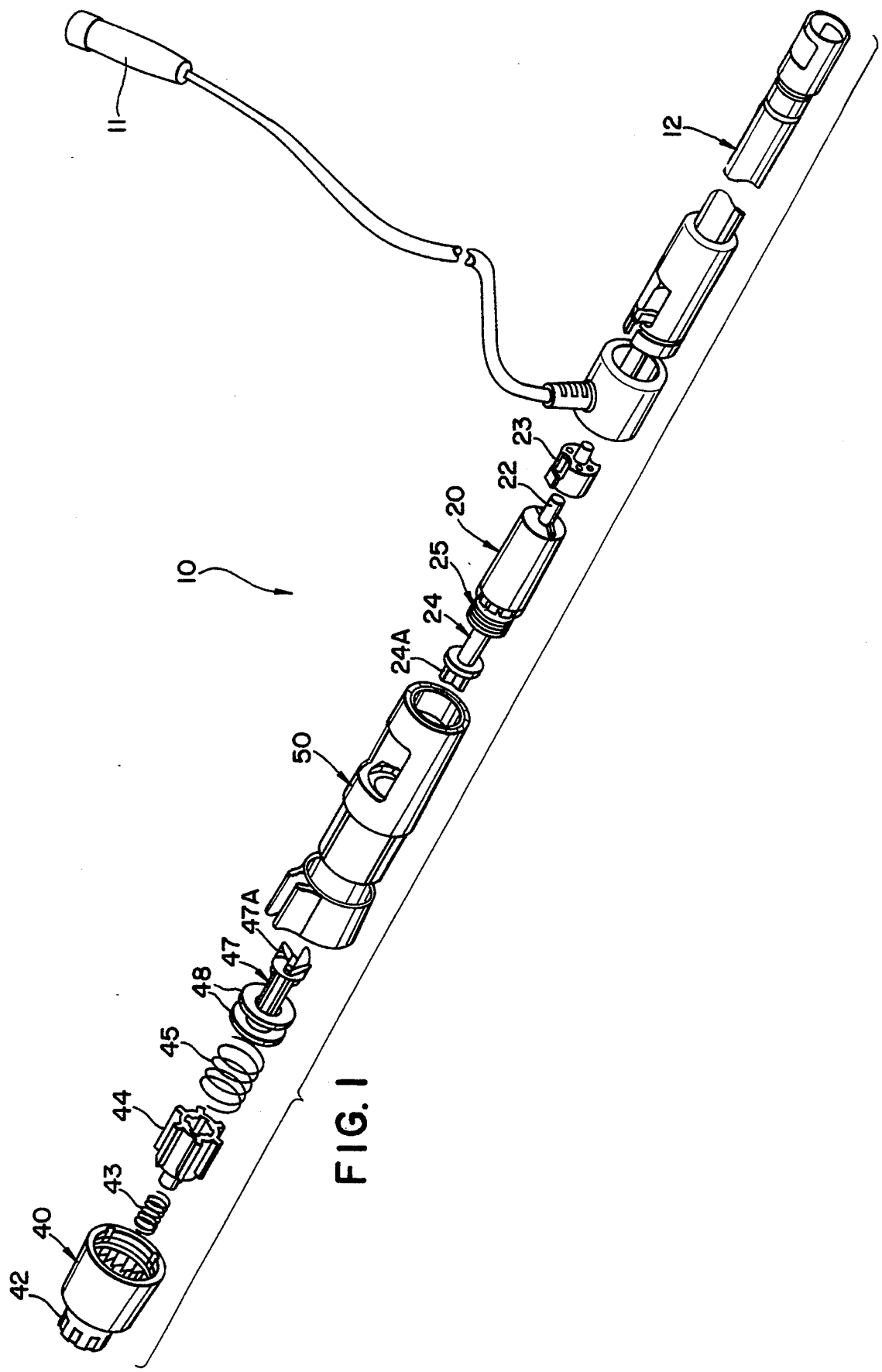
FIG. 1 is an exploded perspective view of one embodiment of a single junction reference half cell electrode.
Figure 2:
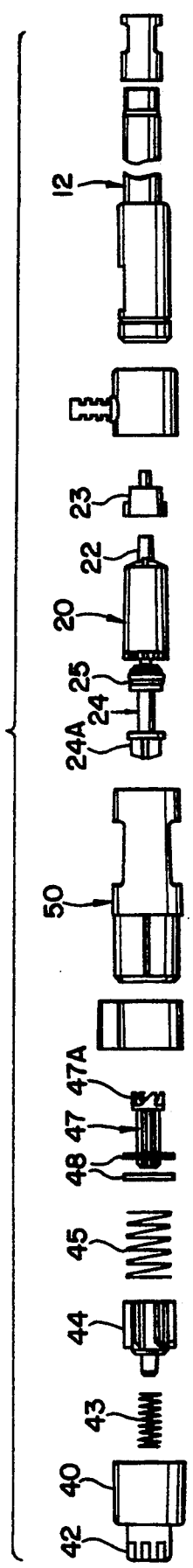
FIG. 2 is an exploded side elevational view of the embodiment of electrode shown in FIG. 1.
Figure 3:
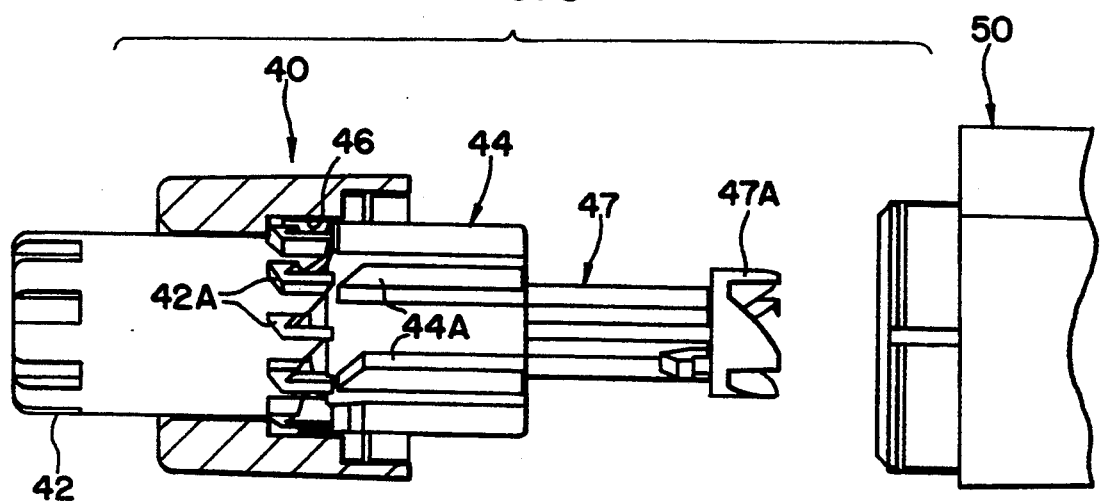
FIG. 3 is a side-elevational, partially cut-away view of the actuator mechanism which is useful in this invention.
Figure 5:
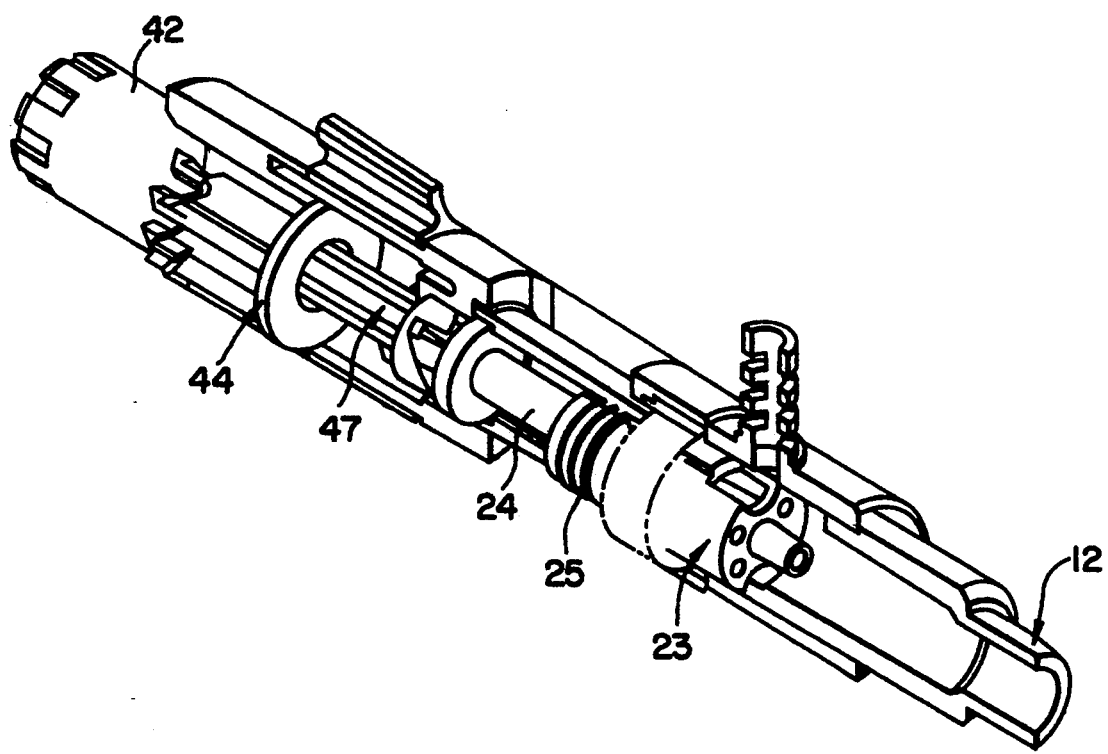
FIG. 5 is a cut-away view of the upper portion of the reference electrode of FIG. 1.

In FIGS. 1-8 there is shown one embodiment of reference electrode 10 of the invention. This is a single junction reference half cell electrode which includes an elongated body member 12 and a removable cartridge 20 at the upper end of the electrode.

The cartridge contains a supply or reservoir of flowable gel electrolyte which can be dispensed when needed into one end of an elongated tube 30 carried by the barrel or body member 12. The cartridge is manufactured such that it can be sealed and stored for extended periods, without leaking, until it is required to be used. The preferred cartridge is shown in cross-section in FIG. 7.

One end of the cartridge includes a neck portion 22 with an opening 22A at the end. The neck portion is inserted into an adaptor 23 having a neck portion 23A which fits onto one end of tube 30 where it is frictionally engaged. A threaded shaft 24 extends through the cartridge. A piston 25 is positioned in the cartridge and it threadably engages the piston. The piston is prevented from rotating within the cartridge.

In order to cause the piston to move toward the open end of the cartridge, it is necessary to rotate the shaft 24. This can be done by means of an actuator 40. In this embodiment the piston is oval in cross-section and it is adapted to move longitudinally in an oval-shaped cartridge bore. This non-circular shape for the piston and the cartridge prevents the piston from rotating as it is moved longitudinally through the cartridge to cause the electrolyte to be dispensed through the neck portion and out the open end. Other complementary, non-circular cross-sectional shapes for the piston and the cartridge could also be used, if desired.

A rubber gasket or seal 21 is preferably carried by the periphery of the piston so as to form a seal between the piston and the interior surface of the cartridge. The oval shape is preferred as the seal is maintained over a continuous, smoothly-curved surface.

A piston having a circular cross-section could instead be used if driver means are provided to move the piston longitudinally through the cartridge.

The actuator mechanism used herein is intended to translate linear motion of the user's finger on a pushbutton 42 into incremental rotary motion of the threaded shaft 24 on which the piston is carried and which extends through the length of the cartridge. Also, the user can depress the pushbutton past a detent, at which point the pushbutton can be rotated any desired amount for the purpose of causing macro amounts of electrolyte to be dispensed from the cartridge. This is illustrated in FIG. 8B. Thus, instead of the normal incremental dispensing that occurs by depressing the pushbutton, the shaft can be rotated rapidly for purging electrolyte through the line. When the pushbutton is operated, the rotary motion of the actuator crown is transmitted directly through a coupling 47 to the threaded shaft. The operation of the shaft is as follows:

1. The user depresses the plunger (i.e., pushbutton) approximately 0.25 inch, fully compressing the small spring 43 and forcing the crown 44 downward.
2. As the crown is forced downward the large spring 45 is compressed, resulting in a return force on the crown.
3. For the initial 0.10 inch of downward movement, both the crown and the plunger are prevented from rotating by being captured by the bosses 46 in the upper housing.
4. As the crown is pushed out of the bosses in the upper housing, the return force of the large spring forces the bevels (bosses 44A) of the crown to slide along the bevels (bosses 42A) of the plunger. The force of the spring acting along these edges forces the crown to rotate until it contacts the trailing edges of the bosses on the plunger. This motion results in a "snapping" action which provides tactile and aural feedback to the user that the downward motion is completed. The washer 48 acts as a bearing surface for the large spring, as does the lower face of the crown. By using materials for these pieces with low coefficients of friction (e.g., teflon and teflon-filled polycarbonate) less rotational drag is induced on the rotating parts, increasing the efficiency of the mechanism.
5. At this point the user releases the plunger and the return pressure of both springs forces the plunger into its fully-retracted position.
6. As the plunger moves higher into the upper housing, the bevels 46 on the housing contact the bevels 44A on the crown. This releases the crown from the plunger and forces it to continue to rotate until the bosses of the crown are aligned with the grooves in the upper housing.
7. The crown then follows the plunger upward until it is in the fully-retracted position, now having completed one segment of its revolution. The amount of this rotation is limited by the number of boss sets on the plunger and upper housing. For example, the actuator illustrated here rotates the crown thirty degrees for each operation by having twelve sets of bevels.

Figure 6:
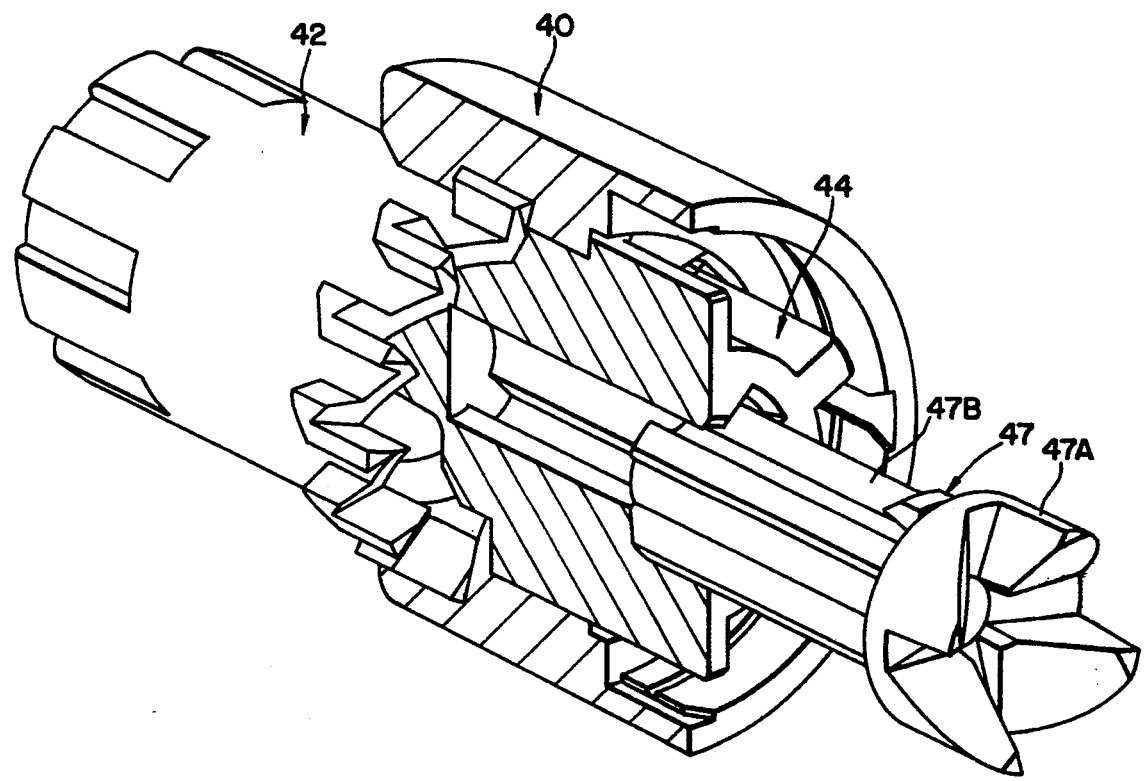
FIG. 6 is a cut-away view of the actuator mechanism used in the reference electrode of FIG. 1.

As shown in FIG. 6, the ribs 47B on the coupling 47 are splined in the crown 44 so that rotational movement of the crown causes corresponding rotational movement of the coupling.

The lower housing 50 contains the chamber for the disposable cartridge, the attachment mechanism for the electrode body (a threaded body in this case), and the coupling to translate the rotation of the crown to the threaded shaft. The crown is free to slide along the axis of the coupling, while any rotation of the crown is transmitted to the coupling. The lower end 47A of coupling 47 engages the upper end 24A of threaded shaft 24. In this example the actuator parts, other than the springs, are formed of injection molded plastics. The choices of the materials are dependent on the operating environment and good design practice (i.e., pieces that move against each other are commonly formed of different materials).

The amount of electrolyte gel dispensed per operation is dependent upon the number of bevel sets in the actuator, the cross-sectional area of the piston, and the pitch of the threaded shaft. In this case the 12 bevel set actuator, a 10-48 pitch shaft, and the piston are designed to deliver approximately 5 micro-liters of gel per dispensation.

Other types of actuators could be used to drive such a threaded piston. Examples would be:
1. A simple thumbscrew attached to the shaft. This could incorporate a detent providing tactile and aural feedback to the user.
2. Other types of pushbutton mechanisms, such as a pushbutton operating at 90° to the shaft axis.
3. Ratchet and pawl type mechanisms.

Thus, the gel electrolyte is expelled or dispensed from the cartridge by the floating piston. The threaded shaft 24 on which the piston is mounted is turned in fractional revolutions by the pushbutton actuator, such that only several microliters of gel are expelled with each push of the actuator.

When the gel electrolyte exits the cartridge through the open end 22A, it travels through adaptor 23 and down through the delivery tube 30 and contacts a silver chloride coated silver wire 36 which extends into the lower end of the tube a short distance (e.g., 0.75 inch). The lower end of the wire 36 is soldered to the electrical shield 35 which is connected to one lead in plug 11. Another silver wire 39 terminates at its lower end in glass bulb 38, and its upper end is connected to another lead in plug 11 for connection to a meter.

The tubes 30 and 32 are composed of inert material (e.g., Teflon or PEEK) so that they are not attacked by the sample being tested and so that crystal growth is avoided. Reactive plastics would provide binding sites for ions in solutions.

The diameter of the tubing is large enough to prevent clogging and fouling and yet is small enough to prevent excessive contamination of the sample with electrolyte. Generally, the diameter of the tubing is in the range of 0.01 to 0.05 inch (inside diameter). The flow of the electrolyte loops is at least 360° before it exits the body member 12 as an added precaution to prevent reference element contamination in the event that the electrode is left for extended periods of time in a deleterious sample.

In the embodiment shown in FIGS. 4A and 4B, there are two separate tubes 30 and 32. The lower end of tube 30 terminates below the upper end 32A of tube 32. The gel flows out through the lower end of tube 30 and fills teflon chamber 33 before it enters the upper end of tube 32, after which it flows downwardly to the open end 32B, as shown by arrows in FIG. 4B.

It is necessary for tube 32 to have a smaller diameter than tube 30 so that a positive force is required in order to force the gel through tube 32. The lower end of tube 32 extends through a plug 37 at the lower end of the electrode.

The composition of the electrolyte is typical of most reference electrode electrolytes with the addition of a non-ionic gelling agent. Hydroxyethylcellulose works well for this application, as it forms a consistent gel even at high salt concentrations. Pseudoplastic properties of the gel are also desirable, as they allow the gel to be easily pumped and yet allow it to retain its high viscosity during the measurement phase of its operation. By pseudoplastic is meant that the gel becomes less viscous when under shear (e.g., when being pumped) but becomes more viscous when static.

The static viscosity of the electrolyte gel is preferably greater than about 2000 cps. and yet remains flowable. Other suitable gelling agents which may be used include polyethyleneoxide or hydroxymethylcellulose.

Operation of the electrode begins by inserting the reference electrolyte cartridge into the actuator housing, and then attaching the cartridge and housing to the electrode body. The tubing is then purged of air by pushing the actuator several times until gel emerges from the outlet tube 32. Alternatively, the purging can be performed by rotating the pushbutton in the manner described above. Usually, the electrode sensor is then calibrated in appropriate standards. To take a measurement, the pushbutton actuator is pushed once, the electrode tip(s) is rinsed and then placed in the sample. The potential reading is recorded when it is stable. To take another measurement, the same procedure is followed. This continues until the gel cartridge is empty, at which time the cartridge is removed and replaced with a new one. The cartridge may be kept inside the assembled electrode for several weeks without use, and not have to be removed. For longer periods without use the cartridge can be removed and sealed, and the delivery tube inside the electrode body purged of gel to prevent clogging.

The same principle of operation for the single junction Ag/AgCl reference half cell can be applied to: i) reference half cells which use other metal/metal salt reference elements, ii) double junction reference half cells, where the gel contacts an internal reference electrolyte instead of a metal/metal salt reference element, iii) combination potentiometric sensors, where the reference half cell is embodied in the same housing as the measuring half cell (e.g., pH or ion selective electrodes, e.g., $NO_3^-$, $F^-$, $K^+$, $Ca^{+2}$, etc.). Also, the principle of operation can be applied to other metal/metal salt reference elements (e.g., $Pb/PbSO_4$, Ag/AgBr, Ag/AgI, etc.).

In the embodiment shown in FIG. 9 the gel electrolyte proceeds through a single tube 60 which includes a loop 60A therein. The wire 62 is soldered at its lower end 62A to electrical shield 35 which is connected to one lead in a connection plug. The opposite end of wire 62 passes into tube 60 at a point above the loop and extends downwardly in tube 60 to a point below the top of the loop. The other silver wire 39 terminates in the glass bulb 38 and is connected at its other end to another lead in the connection plug.

The tube arrangement for conducting electrolyte gel from the gel cartridge to the lower end of the electrode is shown in two different versions or embodiments in the drawings. One version is the single continuous tube 60 (FIG. 9) and the other version is the double tube combination 30 and 32 (shown, for example, in FIGS. 4A and 4B). For purposes of this invention these versions are considered equivalent. The version of FIG. 9 includes a tube with an integral loop of at least 360°.

The version of FIGS. 4A and 4B (with tubes 30 and 32 and reservoir or chamber 33) is also considered to include a loop of at least 360° because the gel flow path must make a loop in order to flow from tube 30 to tube 32.

Other variants are possible without departing from the scope of this invention.

What is claimed is:

1. A reference electrode comprising:
   (a) an elongated body member;
   (b) an elongated tube supported by said body member; said tube including first and second ends; wherein said tube includes a loop of at least 360° between said first and second ends; wherein said second end is open;
   (c) a wire electrode positioned in said tube; and
   (d) a supply of flowable gel electrolyte which is in communication with said first end of said tube; wherein said electrolyte fills said tube and is in contact with said electrode.

2. A reference electrode in accordance with claim 1, wherein said supply of gel electrolyte is contained in dispensing means, comprising a cartridge.

3. A reference electrode in accordance with claim 2, wherein said cartridge includes a piston and actuator means for moving said piston in said cartridge.

4. A reference electrode in accordance with claim 3, wherein said cartridge further includes a threaded shaft extending therethrough; wherein said piston threadably engages said threaded shaft; and wherein said actuator means is rotates said threaded shaft relative to said piston.

5. A reference electrode in accordance with claim 4, wherein said actuator means comprises:
   (a) a cylindrical tubular housing having internal bosses;
   (b) a plunger extending into said housing and is axially moved within said housing; wherein said plunger includes external bosses;
   (c) a crown member axially moves in said housing and translates axial movement of said plunger to rotary motion of said crown member; and
   (d) a coupling between said crown member and said threaded shaft for transferring rotary motion of said crown member to said threaded shaft.

6. A reference electrode in accordance with claim 1, wherein said wire electrode comprises silver and said electrolyte comprises a non-ionic gelling agent, potassium chloride, silver chloride, and water.

7. A reference electrode in accordance with claim 1, wherein said wire electrode comprises a metal and said electrolyte comprises a salt of said metal.

* * * * *